US011793951B2

(12) United States Patent
O'Flaherty et al.

(10) Patent No.: US 11,793,951 B2
(45) Date of Patent: **\*Oct. 24, 2023**

(54) AUTOMATIC DISPENSER FOR RESPIRATORY DELIVERY DEVICE AND METHOD

(71) Applicant: De Motu Cordis Pty Ltd, Queensland (AU)

(72) Inventors: Brendan O'Flaherty, Wilston (AU); Johann Lipman, Wilston (AU); Patrick Joseph Lynch, Wilston (AU); John Fredatovich, Wilston (AU)

(73) Assignee: DE MOTU CORDIS PTY LTD, Queensland (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/619,190

(22) PCT Filed: Jun. 23, 2020

(86) PCT No.: PCT/AU2020/050633
§ 371 (c)(1),
(2) Date: Dec. 14, 2021

(87) PCT Pub. No.: WO2020/257845
PCT Pub. Date: Dec. 30, 2020

(65) Prior Publication Data
US 2022/0305222 A1    Sep. 29, 2022

Related U.S. Application Data

(63) Continuation-in-part of application No. 16/450,077, filed on Jun. 24, 2019, now Pat. No. 10,828,432.

(51) Int. Cl.
*A61M 15/00*    (2006.01)

(52) U.S. Cl.
CPC .... *A61M 15/0041* (2014.02); *A61M 15/0008* (2014.02); *A61M 15/0025* (2014.02); *A61M 15/0035* (2014.02); *A61M 2202/064* (2013.01)

(58) Field of Classification Search
CPC .............. A61M 15/00; A61M 15/0001; A61M 15/0005; A61M 15/0006; A61M 15/0008;
(Continued)

(56) References Cited

U.S. PATENT DOCUMENTS 3,518,992 A * 7/1970 Howell ............. A61M 15/0041
128/203.15
3,795,244 A * 3/1974 Lax .................. A61M 15/0033
128/203.15
(Continued)

FOREIGN PATENT DOCUMENTS

DE        19825434        8/1999
GB        2418147         3/2006
(Continued)

OTHER PUBLICATIONS

Merriam Webster Definition of the term "cap".*
(Continued)

*Primary Examiner* — Colin W Stuart
(74) *Attorney, Agent, or Firm* — Hoffmann & Baron, LLP

(57) ABSTRACT

The present invention provides a particulate delivery device with an automatic activation mechanism that pierces or cuts a composition capsule when a cap is removed. The cap cannot be replaced once the device is activated for use. The device allows for gas flow through the device from a gas inlet to a gas outlet through a composition receptacle and dispersion chamber to deliver particulate to the airway of a subject.

19 Claims, 14 Drawing Sheets

(58) Field of Classification Search
CPC .......... A61M 15/0021; A61M 15/0025; A61M 15/0028; A61M 15/003; A61M 15/0033; A61M 15/0035; A61M 15/0036; A61M 15/0038; A61M 15/0041; A61M 15/0081; A61M 2205/27; A61M 2205/273; A61M 2202/064

See application file for complete search history.

(56) References Cited

U.S. PATENT DOCUMENTS

| | | | |
|---|---|---|---|
| 3,837,341 A * | 9/1974 | Bell | A61M 15/0028 128/203.15 |
| 3,991,761 A * | 11/1976 | Cocozza | A61M 11/003 128/203.15 |
| 4,249,526 A * | 2/1981 | Dean | A61M 15/0033 128/203.15 |
| 4,423,724 A * | 1/1984 | Young | A61M 15/0033 128/203.15 |
| 5,201,308 A | 4/1993 | Newhouse | |
| 5,239,992 A | 8/1993 | Bougamont et al. | |
| 5,355,873 A | 10/1994 | Del Bon et al. | |
| 5,507,281 A | 4/1996 | Kuhnel et al. | |
| 5,619,985 A | 4/1997 | Ohki et al. | |
| 5,727,546 A | 3/1998 | Clarke et al. | |
| 5,989,217 A | 11/1999 | Ohki et al. | |
| 6,766,799 B2 | 7/2004 | Edwards et al. | |
| 7,107,988 B2 | 9/2006 | Pinon et al. | |
| 7,353,823 B2 | 4/2008 | Tsutsui | |
| 8,327,842 B2 | 12/2012 | von Schuckmann | |
| 8,550,073 B2 | 10/2013 | Djupesland | |
| 10,828,432 B1 | 11/2020 | O'Flaherty et al. | |
| 2003/0000523 A1 * | 1/2003 | Citterio | A61M 15/0028 128/203.15 |
| 2003/0079743 A1 | 5/2003 | Genova | |
| 2003/0106550 A1 | 6/2003 | Harvey | |
| 2004/0035421 A1 | 2/2004 | Schuckmann | |
| 2004/0107963 A1 | 6/2004 | Finlay et al. | |
| 2004/0206350 A1 * | 10/2004 | Alston | A61M 15/0033 128/203.12 |
| 2007/0283955 A1 | 12/2007 | Tsutsui | |
| 2007/0295332 A1 * | 12/2007 | Ziegler | A61M 15/0033 128/203.15 |
| 2008/0105256 A1 * | 5/2008 | Lulla | A61M 15/0028 128/203.21 |
| 2009/0194105 A1 | 8/2009 | Besseler et al. | |
| 2009/0320838 A1 | 12/2009 | Malhotra et al. | |
| 2011/0126830 A1 | 6/2011 | Djupesland | |
| 2015/0165138 A1 | 6/2015 | Mayer | |
| 2016/0158470 A1 * | 6/2016 | Esteve | A61M 15/0041 128/203.15 |
| 2016/0279355 A1 * | 9/2016 | Malhotra | A61M 15/0025 |
| 2018/0207370 A1 * | 7/2018 | Rowland | A61M 15/002 |

FOREIGN PATENT DOCUMENTS

| | | |
|---|---|---|
| WO | 2007/144659 A1 | 12/2007 |
| WO | 2008/034504 | 3/2008 |
| WO | 2008/053253 A2 | 5/2008 |
| WO | 2009/059894 | 5/2009 |
| WO | 2013/087788 | 6/2013 |
| WO | 2014/058208 | 4/2014 |
| WO | 2016/115379 | 7/2016 |
| WO | 2018/204217 | 11/2018 |
| WO | 2020/257843 | 12/2020 |

OTHER PUBLICATIONS

Merriam Webster Definition of the term "remove".*
International Search Report for PCT/AU2020/050633, dated Sep. 1, 2020.
Written Opinion for PCT/AU2020/050633, dated Sep. 1, 2020.
International Search Report for PCT/AU2020/050606, dated Jul. 14, 2020.
Written Opinion for PCT/AU2020/050606, dated Jul. 14, 2020.

* cited by examiner

AUTOMATIC DISPENSER FOR RESPIRATORY DELIVERY DEVICE AND METHOD

FIELD OF THE INVENTION

The present invention relates to a respiratory delivery device. More specifically, the invention relates to an automatic dispenser for a delivery device for use in administering particulate medicament to a subject's airway.

BACKGROUND OF THE INVENTION

For some medical conditions, it can be desirable to administer medicament to a subject via the airways. Inhalers, such as dry powder inhalers, can be used for this purpose, as can insufflators.

Existing inhalers typically have poor reliability and/or repeatability in regard to delivered dose, with dosage generally affected by variation in subject inhalation. This typically restricts the use of inhalers to applications wherein variation in dosage is tolerable, e.g. where effects of substantial under and/or over-dosing are not life-threatening.

Accordingly, new strategies for respiratory administration of medicament would be desirable. It would be particularly desirable to develop new respiratory delivery devices offering improved versatility or flexibility in use.

SUMMARY OF INVENTION

In a first aspect, the invention provides a device for delivery of a composition to an airway of a subject, the device comprising:
  in fluid communication:
    a gas inlet;
    a gas outlet;
    a composition receptacle adapted to receive a composition capsule containing the composition; and
    a dispersion chamber; and
  one or more primers adapted to pierce the composition capsule to release the composition upon removal of a cap.

Each primer suitably comprises a cam follower activated by a cam on the cap to move a pin or blade to pierce or cut the composition capsule.

The cam follower is preferably elastically deformable.

Preferably the cam followers of the one or more primers prevent the cap from being replaced once removed.

In one form, the cap comprises a cap top movable relative to the cap with one or more elongate members extending from the cap top and adapted to hold the composition capsule in place.

The dispersion chamber is suitably adapted to receive the composition for delivery to the subject and to disperse the composition into gas flow between the gas inlet and the gas outlet, for delivery to the airway of the subject.

Preferably the dispersion chamber is adapted to promote movement of the composition capsule within the dispersion chamber. Suitably the movement is rotational movement or spinning of the composition capsule.

The dispersion chamber may be continuous with one or more chamber ports through which gas flows between the gas inlet and the gas outlet.

The dispersion chamber may comprise one or more protrusions projecting from a surface thereof. The protrusions or projections facilitate dispersion of the composition. The one or more protrusions comprise one or more of elongate protrusions, radially oriented bumps or protuberances on a surface of the dispersion chamber. Preferably, there is provided at least two protrusions, bumps or protuberances. The protrusions, radially oriented bumps or protuberances may project from a wall or ceiling of the dispersion or vortex chamber. Suitably, the composition capsule is displaced by the one or more protrusions, bumps or protuberances during its rotational movement to assist dispersion of the composition. Typically, the height of the radially oriented bumps or protuberances, beyond the surface from which they project, is between about 0.1 mm and about 1 mm, inclusive of 0.2, 0.3, 0.4, 0.5, 0.6, 0.7, 0.9, and 0.9 mm.

Suitably the dispersion chamber is a vortex chamber with gas flow through the one or more chamber ports facilitating production of a vortex within the vortex chamber.

The device preferably further comprises a deagglomerator located substantially adjacent to the dispersion chamber and in fluid communication with the gas inlet, gas outlet, composition receptacle and dispersion chamber.

The deagglomerator may comprise a screen or mesh. Suitably, the screen or mesh comprises a plurality of holes or slots to promote gas turbulence. The deagglomerator further functions to filter the composition to remove debris from the composition capsule including fragments thereof.

In one form the deagglomerator may comprise one or more flexible members. Suitably, the flexible members are adapted to vibrate in response to gas flow between the gas inlet and the gas outlet.

The gas inlet may be in the form of a base having one or more holes for ingress of gas and a capsule seat adapted to locate the composition capsule in the composition receptacle. The holes may be sealed by removable plugs. Suitably, the plugs must be removed before the cap can be removed.

In one form, the composition capsule is held in place for piercing by the one or more primers between the capsule seat formed in the base comprising the gas inlet and the one or more elongate members extending from the cap top of the cap.

The gas outlet is suitably sized and shaped as a mouthpiece.

Suitably, gas flow between the gas inlet and the gas outlet facilitates delivery of the composition to the airway of the subject, via the gas outlet.

The device is preferably sealed, or substantially sealed to the entry and/or exit of gas except by the gas inlet and the gas outlet.

In another aspect the invention resides in a method of administering a composition to the airway of a subject using the device described above when loaded with a composition capsule substantially inside the composition receptacle, including the steps of:
  moving the cap so that cams on the cap engage cam followers on the one or more primers thereby causing the primers to pierce or cut the composition capsule;
  removing the cap so as to uncover the gas outlet and release the primers; connecting the gas outlet with the airway of the subject; and
  providing gas flow between the gas inlet to the gas outlet, such that the composition is delivered by the gas flow to the airway of the subject via the gas outlet and thereby administer the composition to the airway of the subject.

Suitably inhalation through the gas outlet by a subject causes gas flow from the gas inlet that moves the composition capsule from the composition receptacle to the dispersion chamber.

Preferably the cap cannot be replaced once removed.

In a further aspect there is provided a method of treating or preventing a condition in a subject by administering an effective amount of composition to the airway of a subject using the device described herein, including the steps of:

placing the composition capsule substantially inside the composition receptacle;

connecting the gas outlet with the airway of the subject; and providing gas flow from the gas inlet to the gas outlet, whereby the composition is delivered by the gas flow to the airway of the subject via the gas outlet, to thereby treat or prevent the condition in the subject.

In this specification, the terms "comprises", "comprising", "includes", "including", or similar terms are intended to mean a non-exclusive inclusion, such that a method, system or apparatus that comprises a list of elements does not include those elements solely, but may well include other elements not listed.

It will be appreciated that the indefinite articles "a" and "an" are not to be read as singular indefinite articles or as otherwise excluding more than one or more than a single subject to which the indefinite article refers. For example, "a" gas inlet includes one gas inlet, one or more gas inlets or a plurality of gas inlets.

DETAILED DESCRIPTION OF THE DRAWINGS

Respiratory delivery of therapeutic agents can be suitable for a range of applications. These include applications wherein the subject is typically conscious and responsive, such as administration of powdered vaccines, antibiotics, and insulin; and applications wherein the subject may be unconscious, such as administration of powdered adrenaline for the treatment of critical illnesses such as anaphylaxis or cardiac arrest.

The current invention is at least partly predicated on the realisation that there is a need for a device that offers flexibility for respiratory delivery of therapeutic agents. In particular, devices facilitating both respiratory delivery of compositions under negative pressure, similar as for 'inhaler'-type devices, and respiratory delivery of therapeutic agents under positive pressure, similar as for 'insufflator'-type devices would be desirable, although without limitation thereto.

Without limitation, compositions for delivery referred to herein will typically be in the form of a dry powder. As used herein, and as will be understood by the skilled person, "dry powder" refers generally to a form of particulate medication for respiratory delivery, that is typically delivered, or suitable for delivery, in the absence of propellant.

The composition (e.g. dry powder or particulate medicament) as described herein will suitably comprise at least one "active ingredient", i.e. a component with biological activity. The dry powder or particulate medicament may be in the form of one or more pure, or substantially pure, active ingredients. Alternatively, the dry powder or particulate medicament may include one or more pharmaceutically acceptable components in addition to one or more active ingredients, e.g. fillers, excipients, or diluents, as are well known in the art. For a non-limiting overview of dry powder formulations, the skilled person is directed to Telko and Hickey (2005) 'Dry Powder Inhaler Formulation' Respiratory Care, 50(9), 1209-1227, incorporated herein by reference. It will be appreciated that an active agent and/or a composition containing an active agent may be alternatively referred to as a "drug".

One aspect of the invention provides a device for administering a composition to an airway of a subject. FIGS. 1-3 set forth a typical embodiment of a device of this aspect, device 10.

Figure 1B:
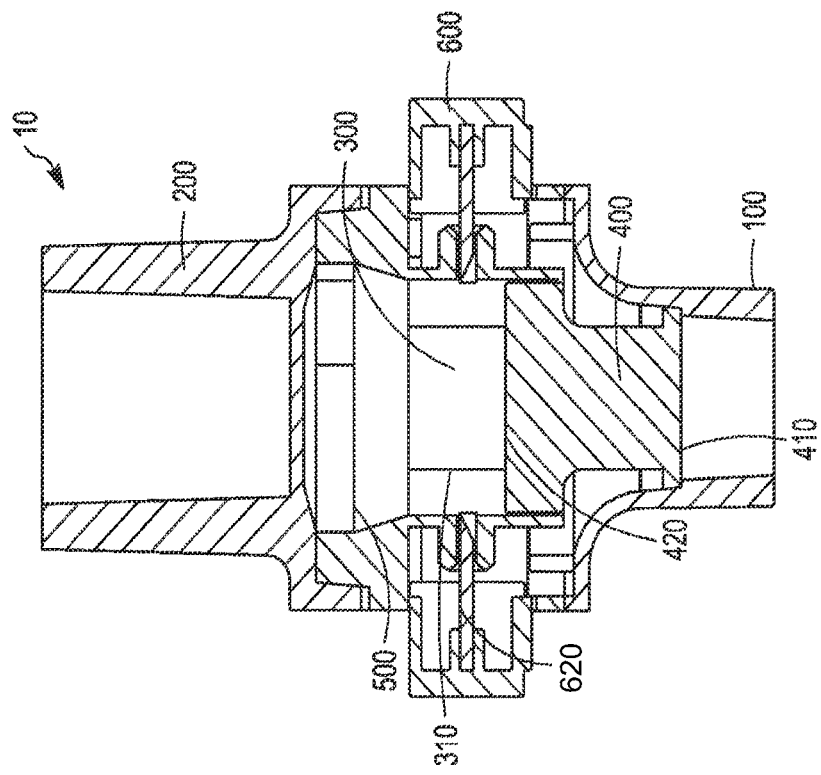
FIG. 1B sets forth a front cross-sectional view of the device of FIG. 1A.
Figure 1A:
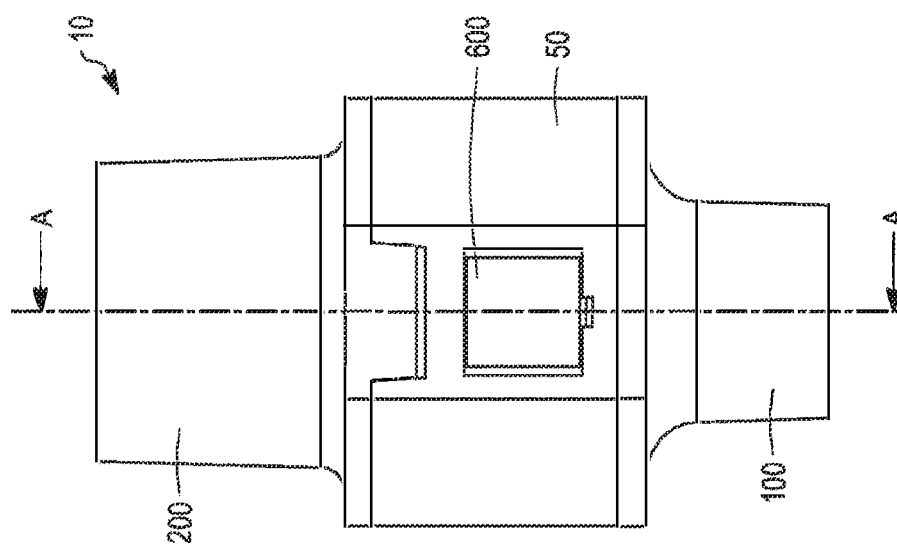
FIG. 1A sets forth a side view of an embodiment of a device of the invention.
Figure 2A:
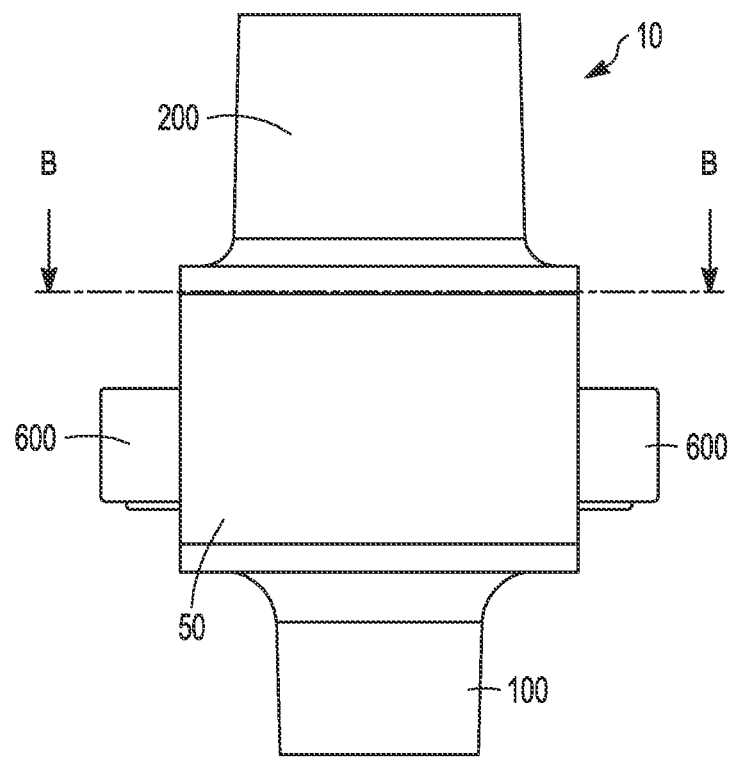
FIG. 2A sets forth a front view of the device of FIG. 1A.

Looking at FIGS. 1A and 1B, device 10 comprises body 50; gas inlet 100; gas outlet 200; composition receptacle 300; actuator 400; dispersion chamber 500; and primers 600.

Figure 2B:
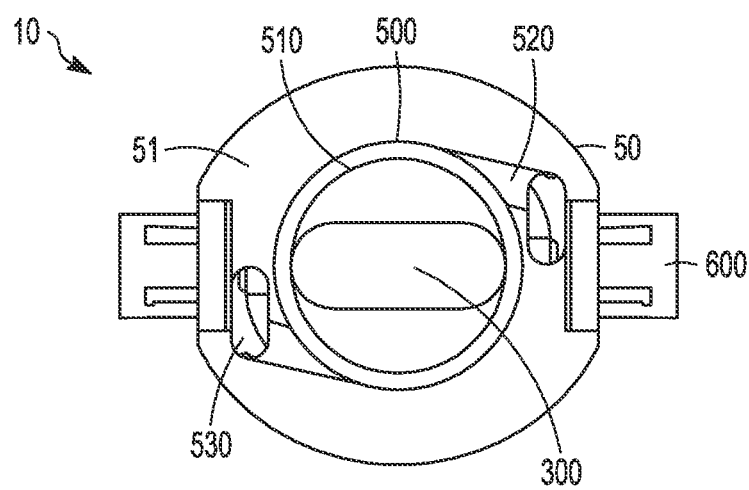
FIG. 2B sets forth a top cross-sectional view of the device of FIG. 1A.

As best seen in FIGS. 1B and 2B, body 50 comprises walls 51 surrounding a hollow inner region. Body 50 is formed from plastic; however, this may be varied as desired. For example, body 50 may be metallic, or comprise rubber. Combinations of suitable materials can also be used.

Gas inlet 100 and gas outlet 200 may be continuous with wall 51 of body 50 although they may be separately constructed.

Gas inlet 100 is adapted for use as a fitting for connecting respiratory equipment, or as a mouthpiece. Similarly, gas outlet 200 is adapted for use as a fitting for connecting respiratory equipment, or as a mouthpiece.

As depicted, gas inlet 100 and gas outlet 200 are conical in shape, which can be desirable for use of as a connection and/or mouthpiece. However, the shape of gas inlet 100 and/or gas outlet 200 can be varied as desired.

Figure 3A:
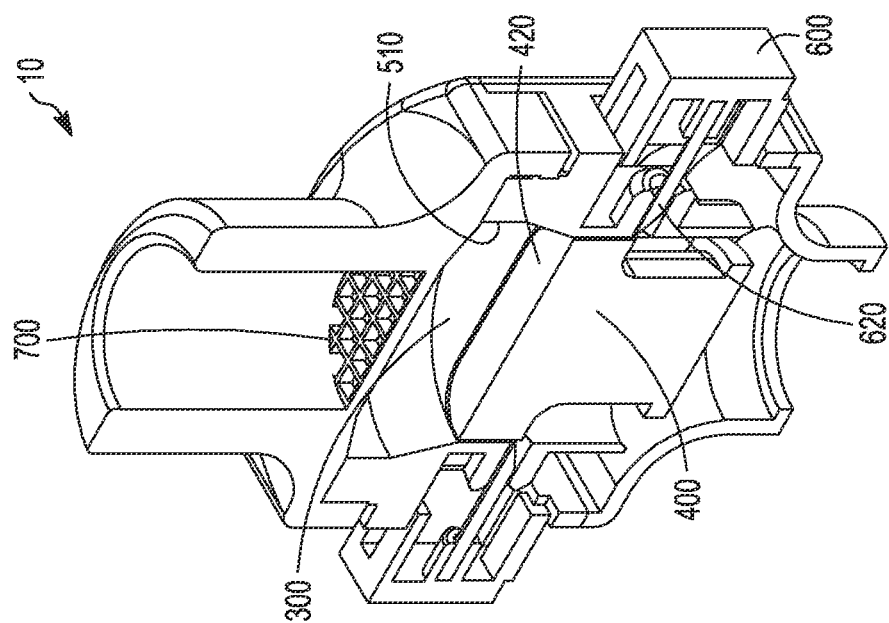
FIG. 3A sets forth a perspective cross-sectional view of the device of FIG. 1A, when the piston is in a first configuration.
Figure 3B:
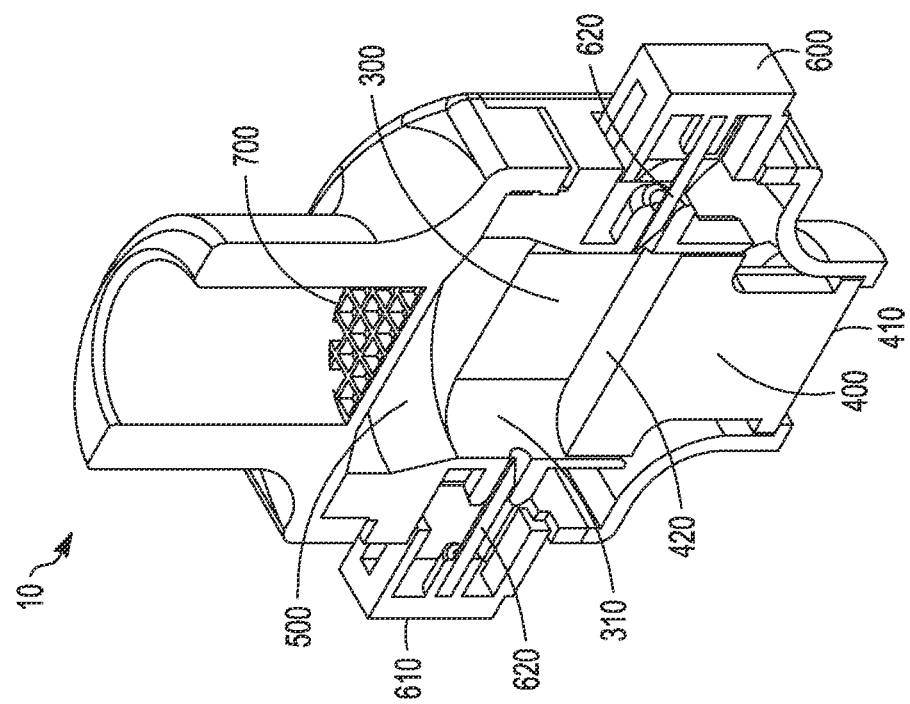
FIG. 3B sets forth a perspective cross-sectional view of the device of FIG. 1A, when the piston is in a second configuration.

As best seen in FIGS. 1B, 3A and 3B, composition receptacle 300 is located within body 50. Composition receptacle 300 of device 10 is in the form of a well, comprising walls 310. Composition receptacle 300 is adapted to fittingly receive a container, such as a capsule, comprising a composition (not shown) to be administered to a subject using delivery device 10.

As best seen in FIG. 1B, actuator 400 is located within body 50. Actuator 400 of device 10 is in the form of a piston, comprising inlet end 410 and outlet end 420. Piston 400 is translatable from a first configuration or position substantially outside of composition receptacle 300, as shown in FIGS. 1B and 3A, to a second configuration or position substantially inside composition receptacle 300 as shown in FIG. 3B, wherein piston 400 is located adjacent or near to dispersion chamber 500. In particular, the outlet end 420 of piston 400 will, in the second configuration, sit closer to the dispersion chamber 500 than it does in the first configuration.

Dispersion chamber 500 of device 10 is in the form of a vortex chamber. As best seen in FIGS. 2B, 3A and 3B, vortex chamber 500 comprises chamber wall 510; chamber channels 520; and associated chamber ports 530 which allow the flow of gas from the gas inlet 100 to the gas outlet 200, and to create and sustain a vortex. In embodiments, vortex chamber 500 may comprise at least a partial ceiling.

Vortex chamber 500 is adapted to receive a container comprising the composition for delivery, upon translation of the container from composition receptacle 300 to vortex chamber 500. Vortex chamber 500 is adapted to allow rotation of the container when located therein, against chamber wall 510.

In embodiments, vortex chamber 500 may comprise one or more protrusions (seen best in FIG. 7) adapted to facilitate dispersion of a composition for delivery from a container comprising the composition. In embodiments, vortex chamber 500 comprises one or more protrusions, radially oriented bumps or protuberances on chamber wall 510 or the chamber ceiling (FIG. 7). Typically, the height of the protrusions, raised portions or radially oriented bumps is between about 0.1 mm and about 1 mm, inclusive of 0.2, 0.3, 0.4, 0.5, 0.6, 0.7, 0.9, and 0.9 mm.

As depicted, device 10 comprises two primers 600, flanking composition receptacle 300. It will be appreciated, however, that a single primer can also be used.

As best seen in FIGS. 1B, 3A and 3B, primers 600 are held within walls 51 of body 50. Primers 600 comprise button 610; and pin 620. Buttons 610 of primers 600 of device 10 may be resilient buttons such as, for example, deformable buttons or spring-loaded buttons, however this can be varied as desired.

It will be appreciated that device 10 is sealed, or substantially sealed, to the entry or exit (e.g. by way of leakage or escape) of gas except by gas inlet 100 and gas outlet 200. As hereinabove described, gas inlet 100 and gas outlet 200 are of or continuous with body 50 of device 10. Additionally, primers 600 are positioned within walls 51 of body 50 in an airtight, or substantially airtight manner.

It will be further understood that devices of this aspect, such as device 10, may comprise a deagglomerator 700 adapted to deagglomerate the composition for delivery to the airway of a subject using the delivery device.

In embodiments of device 10 comprising a deagglomerator 700, typically the deagglomerator 700 is located adjacent or near to dispersion chamber 500 as is best seen in FIGS. 3A and 3B.

In one typical embodiment, the deagglomerator is or comprises a screen or mesh comprising a plurality of holes or slots to promote gas turbulence.

In one typical embodiment, the deagglomerator is or comprises one or more flexible members adapted to vibrate in response to gas flow.

Device 10 is adapted, in use, to entrain a composition in gas flow between gas inlet 100 and gas outlet 200, and deliver the composition entrained in the gas flow to the airway of a subject, via outlet 200.

In use, a container or capsule (not shown) is placed substantially within composition receptacle 300. Typically, the capsule is fittingly held within composition receptacle 300. The container or capsule will suitably comprise a seal or membrane or the like, such as a foil seal or plastic shell, that can be cut or pierced by primers 600. An upper surface of the piston 400 may form the base or floor of the composition receptacle 300.

In use, primer 600 is pressed, which forces pins 620 of primer 600 against a container or capsule placed within composition receptacle 300, piercing or cutting a seal or membrane of the container or capsule.

In use, piston 400 is translated, by gas flow, from the first configuration, as shown in FIG. 3A, wherein composition receptacle 300 is open and accommodates the container or capsule, and inlet end 410 of piston 400 prevents or at least substantially constrains gas flow from gas inlet 100 to gas outlet 200; to the second configuration, as shown in FIG. 3B, wherein outlet end 420 of piston 400 displaces the container or capsule from composition receptacle 300, and gas flow from gas inlet 100 to gas outlet 200 is facilitated or substantially unconstrained by the movement of inlet end 410 of piston 400.

References herein to "substantially unconstrained", in relation to the movement of piston 400 during gas flow, should be understood as being substantially unconstrained flow of gas in relation to the first configuration or position of the piston 400. That is, in the second configuration or position the gas flow will be understood to be constrained to some degree by the paths and channels through which it must flow but the degree of constraint will be significantly less than that experienced when the piston 400 is in the first configuration or position. In embodiments, "substantially unconstrained" may be read as "facilitated", "open", "free" or "clear" flow of gas relative to that when the piston 400 is in the first configuration or position.

In use, piston 400 may be translated from the first configuration to the second configuration by each, individually, of application of negative pressure on piston 400 through gas outlet 200, and application of positive pressure through gas inlet 100.

In one typical scenario, in use, negative pressure is applied to piston outlet end 420 of piston 400 by inhalation of a subject through gas outlet 200, which translates piston 400 from the first configuration to the second configuration.

In one typical scenario, in use, positive pressure is applied to inlet end 410 of piston 400 by exhalation of a user into gas inlet 100, which translated piston 400 from the first configuration to the second configuration.

In one typical scenario, in use, positive pressure is applied to inlet end 410 of piston 400 from a pressurised gas source, such as a gas canister, connected to gas inlet 100, which translates piston 400 from the first configuration to the second configuration.

In use, when piston 400 is translated to the second configuration, displacement of the container or capsule from composition receptacle 300 forces the container or capsule substantially inside vortex chamber 500.

In use, when the container or capsule is located substantially inside vortex chamber 500, flow of gas between gas inlet 100 and gas outlet 200 facilitates dispersion of the composition from the container or capsule.

More particularly, in use, flow of gas between gas inlet 100 and gas outlet 200 enters vortex chamber 500 through chamber channels 520 (which are themselves continuous with chamber ports 530 as best seen in FIG. 7), creating a vortex and causing the container or capsule to rotate within vortex chamber 500. In embodiments, the chamber channels 520 facilitate entry of gas flow into the vortex chamber 500 such that the gas flow path is tangential to or substantially continuous with a wall of the vortex chamber 500.

In use, rotation of the container or capsule within vortex chamber 500 against or near to chamber wall 510 disperses the composition from the container or capsule through the seal or membrane pierced or cut by actioning primer 600 which, in the embodiments of FIGS. 1B, 3A and 3B, will activate pins 620. The protrusions on the chamber wall assist in disrupting the spinning motion of the container due to contact therewith at speed and so assist in promoting the release of composition.

In embodiments of devices of this aspect, such as device 10, further comprising a deagglomerator 700, in use, composition dispersed by vortex chamber 500 is further dispersed and/or deagglomerated by the deagglomerator by flow of gas between gas inlet 100 and gas outlet 200.

In typical embodiments wherein the deagglomerator 700 comprises a screen or mesh, as seen in FIGS. 3A and 3B, comprising a plurality of holes or slots to promote gas turbulence, passage of the composition entrained in gas flow through or past the screen or mesh facilitates further dispersion and/or deagglomeration of the composition by resulting gas turbulence.

In typical embodiments wherein the deagglomerator comprises one or more flexible members adapted to vibrate in response to gas flow, passage of the composition entrained in gas flow through or past the flexible members facilitates further dispersion and/or deagglomeration of the composition by resulting vibration of the flexible member.

In use, composition dispersed by gas flow between gas inlet 100 and gas outlet 200 through or past vortex chamber 500 and, optionally, a deagglomerator of the device, is delivered entrained in the gas flow to the subject's airway.

In one typical scenario, in use, flow of gas between gas inlet 100 and gas outlet 200 past or through vortex chamber 500 and, optionally, a deagglomerator of the device, to deliver the composition entrained in the gas flow to the subject's airway, results from inhalation by the subject through gas outlet 200.

In one typical scenario, in use, flow of gas between gas inlet 100 and gas outlet 200, past or through vortex chamber 500 and, optionally, a deagglomerator of the device, to deliver the composition entrained in the gas flow to the subject's airway, results from exhalation by a user of device 10 into inlet 100.

In one typical scenario, in use, flow of gas between gas inlet 100 and gas outlet 200, past or through vortex chamber 500 and, optionally, a deagglomerator of the device, to deliver the composition entrained in the gas flow to the subject's airway, results from direction of gas from a pressurised gas source, such as a gas canister, into gas inlet 100.

FIGS. 4 through to 8 demonstrate a preferred embodiment of device 10 referred to in these figures as device 1000. It will be appreciated that like parts have like numbering between FIGS. 1 to 3 and FIGS. 4 to 8 and so, for example, actuator or piston 400 in FIGS. 1 to 3 is actuator or piston 1400 in FIGS. 4 to 8; gas inlet 100 is gas inlet 1100 etc. All of the comments made for device 10 are applicable, mutatis mutandis, to device 1000 and are considered to be repeated here in full in relation to device 1000.

FIG. 4 shows the components of device 1000 and the manner in which they are interconnected with actuator or piston 1400 being seated on an inner surface, particularly a lip or flange thereof, of gas inlet 1100; body 1050 connecting with gas inlet 1100 to form a gastight connection; primers 1600 being accommodated within the walls of body 1050 with pins 1620 extending towards the composition receptacle 1300; gas outlet 1200 connecting to body 1050 to form a gastight connection; and, differing to device 10, a cap 1800 to be located over gas outlet 1200.

FIGS. 5A to 7 show in more detail the construction and location of the various components of FIG. 4. It can be seen that the cap 1800 has a well 1810 formed within an upper surface 1820 thereof. From the underside of the cap 1800, beneath the region of the well 1810, there is a downwardly extending elongate member 1830. In the embodiment shown, elongate member 1830 takes the form of prongs or a fork but it will be appreciated a number of other forms could be envisaged which provide for the same outcome. Airflow cannot pass through well 1810 and so the cap 1800 must be removed from device 1000 prior to use.

FIG. 5B is a cross sectional view of device 1000 when the cap 1800 is fully seated or engaged with the gas outlet 1200. In this position an under surface of cap 1800 is substantially in abutment with an upper surface of the gas outlet 1200. Prongs 1830 are seen to extend, in this embodiment, through deagglomerator or screen 1700 (best seen in FIG. 7) and so deagglomerator 1700 has two openings formed therein to allow prongs 1830 to pass through. The openings are of a size such that the functionality of deagglomerator 1700 is substantially not affected by their presence when the cap 1800 is removed and the prongs 1830 are no longer present. The prongs 1830, when the cap 1800 is fully seated, extend into the dispersion chamber or vortex chamber 1500 such that, when a container of composition is seated within the composition receptacle 1300, they act to hold the container in place. This serves to prevent displacement or movement of the container such that it is in an optimal position with respect to the pins 1620 for piercing the container upon removal of the cap.

It can be seen that a lower portion of the walls of the cap 1800 have a chamfered or bevelled portion 1840 which, in the embodiment shown, may be referred to as cam(s) 1840. The buttons, or cam followers, 1610 of primers 1600 are in contact with an upper region of chamfered portions/cam 1840 such that, upon displacing the cap 1800 for removal thereof and use of the device, the chamfer forces an increasing amount of displacement upon the buttons/cam followers 1610 thereby forcing the pins 1620 to extend further into the composition receptacle 1300 and pierce the container of composition which will be located therein. The displacement may be by the pressure exerted on the resilient material forming the buttons/cam followers 1610. This is a distinct advantage of the present invention in that no separate buttons or switches have to be actioned to release the composition. Instead, removal of the cap 1800 automatically results in piercing of the container and release of the composition. Further, the piercing happens only as prongs 1830 are simultaneously being raised and so optimal placement of the container is guaranteed as inward movement of the pins 1620 occurs.

The result of this removal of the cap 1800 can be seen in the change from FIG. 5B to FIG. 6B where the cap 1800 has been raised to the point of maximum displacement of the primers 1600 and so the pins 1620 extend the maximum distance into the composition receptacle 1300. It can also be seen that prongs 1830 are raised and have substantially left the vortex chamber 1500.

Figure 7:
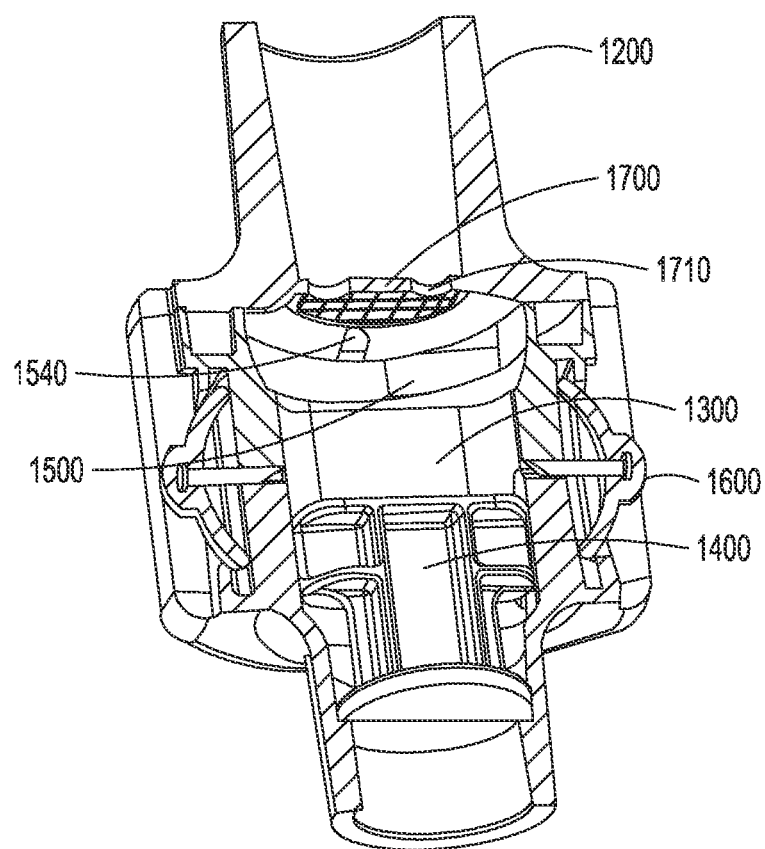
FIG. 7 is a perspective cross-sectional view of the device of FIGS. 5B and 6B with the cap fully disengaged.
Figure 8:
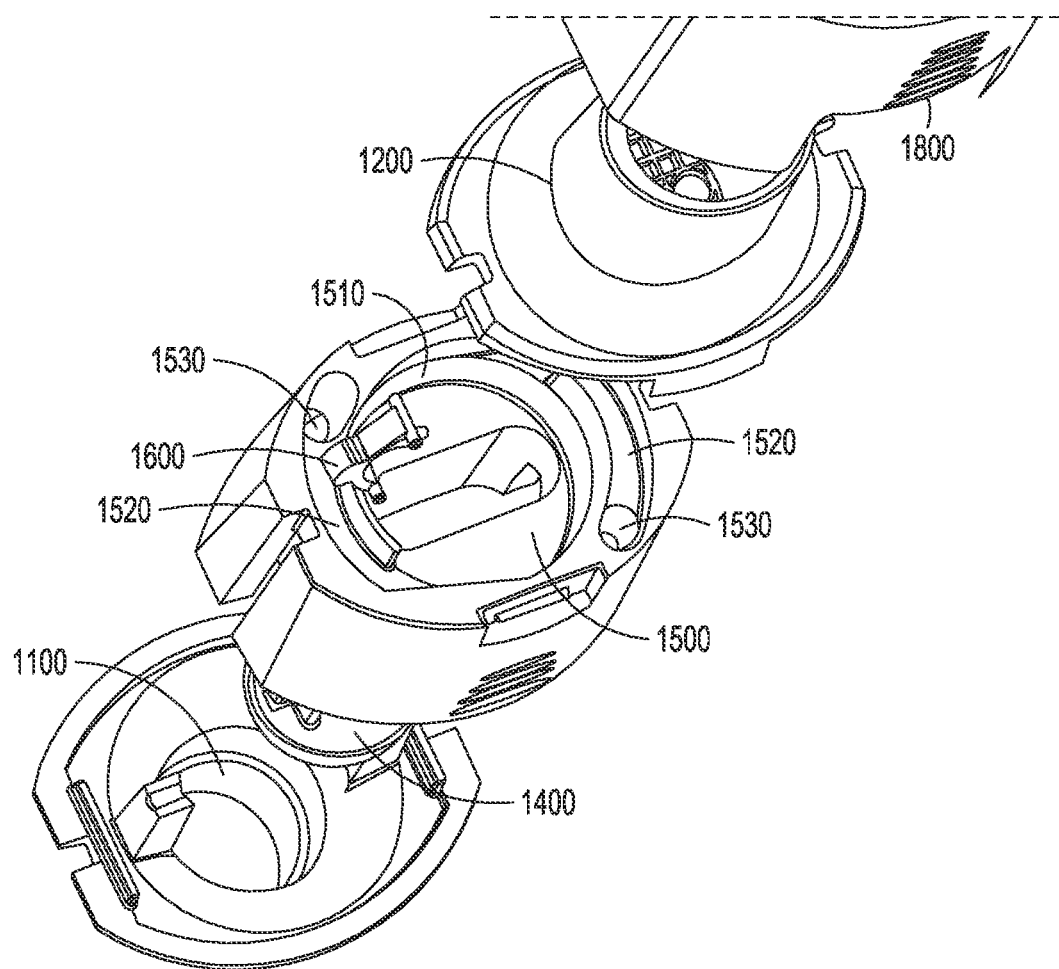
FIG. 8 is a magnified view of a portion of the exploded device of FIG. 4 focusing on certain gas flow pathways.

FIG. 7 shows complete removal of the cap 1800 and so the prongs 1830 are also gone and the openings 1710 in the deagglomerator 1700 can be seen. FIG. 7 also provides a better view of a single protrusion 1540 extending from the vortex chamber 1500 ceiling immediately adjacent the edges of the deagglomerator 1700 which is formed therein. Preferably, there are at least two protrusions 1540 on the vortex chamber 1500 ceiling. It has been found that two such protrusions 1540 which are located at approximately 90 degrees to one another provides for optimal disruption of the motion of the spinning container during use and so optimal release of the composition. That is, if one protrusions 1540 is taken to be positioned at 12 o'clock, then one other is preferably placed at 3 o'clock or 9 o'clock with respect to the first. The protrusions 1540, in the embodiment shown, are elongate protrusions 1540.

In FIG. 7, complete removal of the cap 1800 has also allowed for the primers 1600 to adopt their original positioning and so the pins 1620 have retreated from the composition receptacle 1300. Importantly, it will be appreciated from FIGS. 6B and 7 that once the cap 1800 is removed and primers 1600 revert to their original position, it is not possible to once again simply place the cap 1800 back in full engagement with the device 1000. This is because the chamfered portions/cams 1840 will come into a blocking engagement with an upper surface of the buttons/cam followers 1610. The angle of the chamfer this time works against the displacement of the buttons/cam followers 1610 and so the cap 1800 cannot be lowered any further. This is an advantage of the present device 1000 as it effectively becomes a single use device. If a potential user has a device 1000 with the cap 1800 removed they will immediately know that the device 1000 has been used or the container of composition has otherwise been pierced and is not appropriate for administration. This provides a quick and simple visual queue for a user to know that the device 1000 they are carrying or are provided with is fit for purpose. Given the critical nature of the end medical use in many instances, this is an important safety feature.

It will be appreciated that the piston 1400 in FIGS. 5 to 7 remains unmoved and so no gas is free to flow through the device 1000. However, FIG. 5B can be thought of as a resting or non-use position while FIG. 6B shows a primed position with the container of composition being pierced and FIG. 7 shows a ready to use position whereby the container has been pierced, the cap 1800 has been removed and the device 1000 is ready for a positive or negative pressure to be applied to move piston 1400 from the first configuration to the second configuration, as previously discussed, to enable gas flow from the gas inlet 1100 through to the gas outlet 1200 at which point it will have entrained composition.

FIG. 8 is provided to better demonstrate the gas flow pathway itself. It can be seen that the piston 1400 will normally be seated within the gas inlet 1100 with its inlet end 1410 seated, preferably in a sealing engagement, upon a lip or flange and the container of composition sitting on the upper surface 1420. When the piston 1400 is actuated and moves upwards to displace the container of composition, it will be appreciated that air can then flow past the lip or flange. At this point, the gas flow can continue through chamber ports 1530 which pass through the body 1050 and are continuous with the interior of the gas inlet 1100 and also the vortex chamber 1500. It will be appreciated there may be only one chamber port 1530 but at least two are optimal.

FIG. 8 shows that an upper end of the chamber ports 1530 are continuous with chamber channels 1520 which substantially conform to the walls of the body 1050 such that the entering gas flow is forced into a substantially circular, circulating or vortex pathway. The effect of this is that the container of composition, which has been displaced into the vortex chamber 1500 by movement of the piston or actuator 1400, is caused to spin rapidly. The composition will be released at this stage due to the gas flow and turbulence however, it has been found that release is greatly improved by the presence of the one or more protrusions 1540 into which the container will continually bump or knock thereby causing spilling of composition from the container. The gas flow with entrained composition then passes through deagglomerator 1700 and into the gas outlet 1200 in the manner previously described for device 10.

Device 1000 may be used and connected to equipment or otherwise exactly in the manner described for device 10.

Therefore, in certain embodiments, there is provided a device for administering a composition to an airway of a subject, the device comprising:

a gas inlet, a gas outlet, a piston, a composition receptacle and a dispersion chamber in fluid communication;

the composition receptacle substantially adjacent an upper surface of the piston;

the dispersion chamber located substantially adjacent to the composition receptacle and comprising one or more chamber ports; and a deagglomerator located substantially adjacent to the dispersion chamber;

wherein the piston can be configured between a first configuration wherein the composition receptacle is substantially unrestricted and gas flow between the gas inlet and the gas outlet is constrained; and a second configuration wherein gas flow between the gas inlet and the gas outlet is substantially unconstrained by each, independently, of (i) application of positive pressure via the gas inlet; and (ii) application of negative pressure via the gas outlet.

It will be appreciated that devices of this aspect, such as device 10 and device 1000, can have several important advantages.

Advantageously, embodiments such as device 10 and device 1000 allow for operation under both positive and negative gas flow conditions. Accordingly, device 10 and device 1000 can be used both as an inhaler device, e.g. for self-administration of a composition to the subject by inhalation through gas outlet 200/1200; and as an insufflator device, e.g. for administration of a composition to the subject by the application of positive pressure gas into gas inlet 100/1100 to an unconscious or unresponsive patient.

Advantageously, gas inlet 100/1100 and gas outlet 200/1200 allow for flexibility and versatility in use, with the potential to be used directly as a mouthpiece, or to be used as a connection or fitting for further respiratory equipment.

By way of example, when device 10 and device 1000 are used as an inhaler device, the subject can use gas outlet 200/1200 as a mouthpiece, and inhale directly through gas outlet 200/1200. Alternatively, gas outlet 200/1200 can be used to connect suitable respiratory equipment, such as a mask, inclusive of intraoral masks, oronasal masks, and the like, and advanced airway equipment, such as endotracheal tubes, a supraglottic airways, laryngeal airways, and the like, such as when device 10 and device 1000 are used as insufflator device.

By way of further example, device 10 or device 1000, via gas inlet 100/1100, can be used to connect suitable respiratory equipment, such as a ventilator, a compressed gas supply, a manual resuscitator, and automatic resuscitator, and a demand valve resuscitator, and the like, such as when device 10 or device 1000 is used as an insufflator device. Alternatively, gas inlet 100/1100 can be used directly as a mouthpiece for exhalation into device 10/1000 by a user or caregiver.

Figure 4:
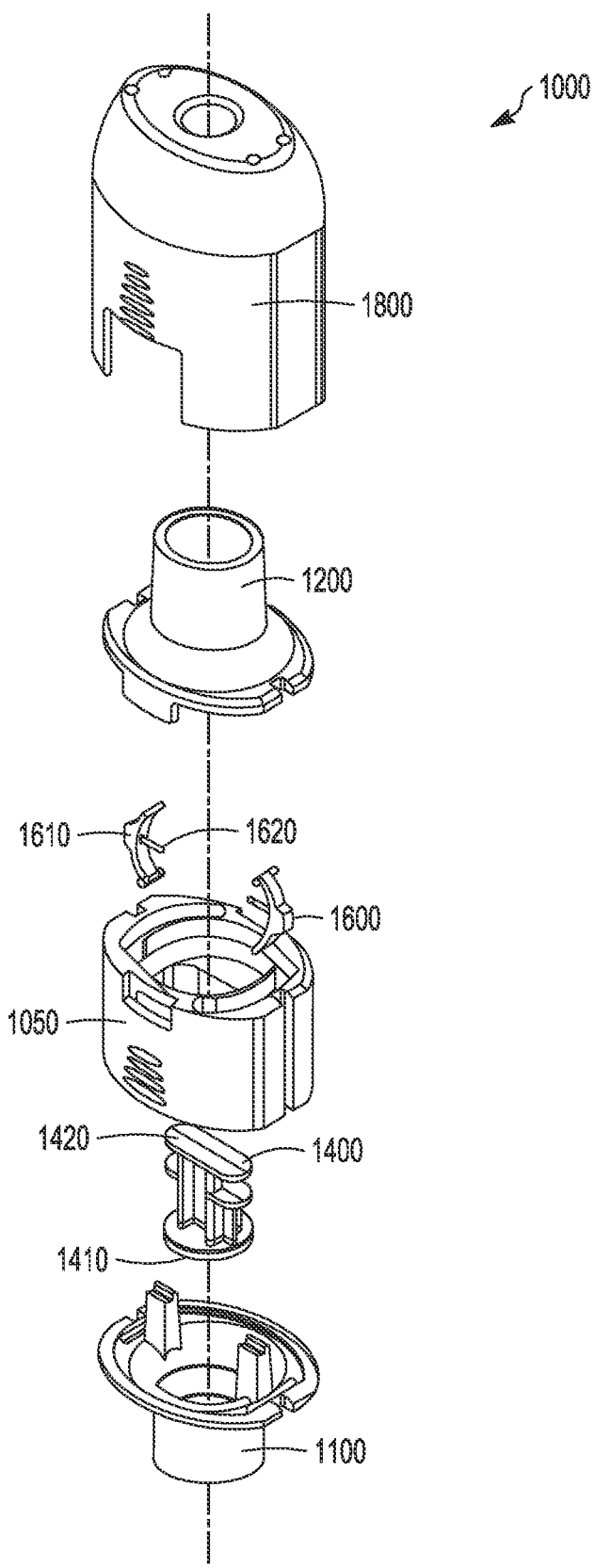
FIG. 4 sets forth an exploded view of a preferred embodiment of a device according to the present invention.
Figure 5A:
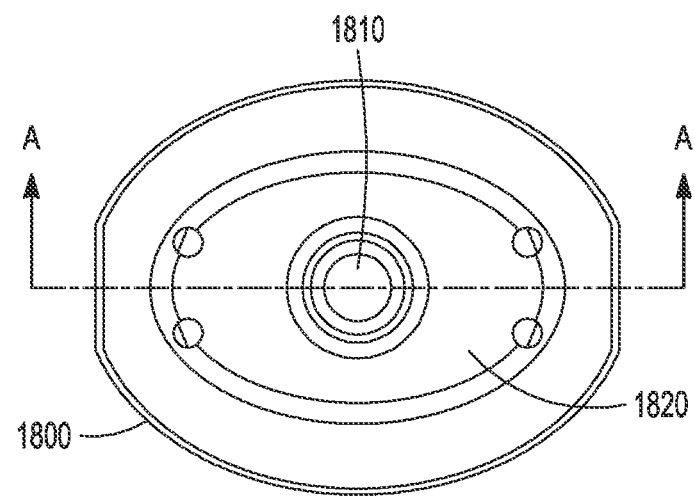
FIGS. 5A and 5B set forth a top cross-sectional view and front cross-sectional view, respectively, of the device of FIG. 4 with the cap fully engaged.
Figure 5B:
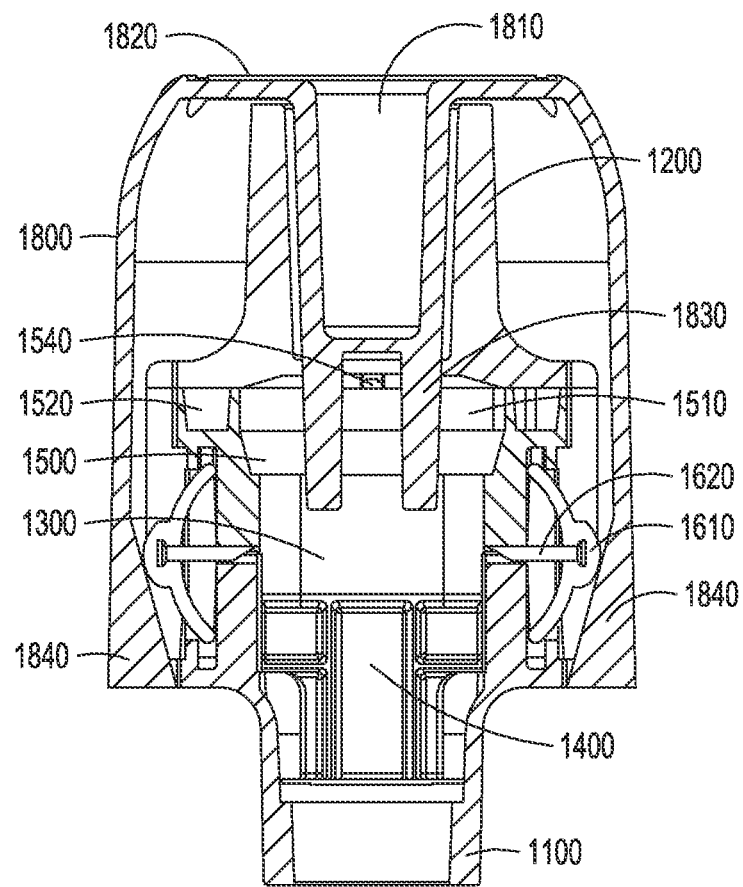
Figure 6A:
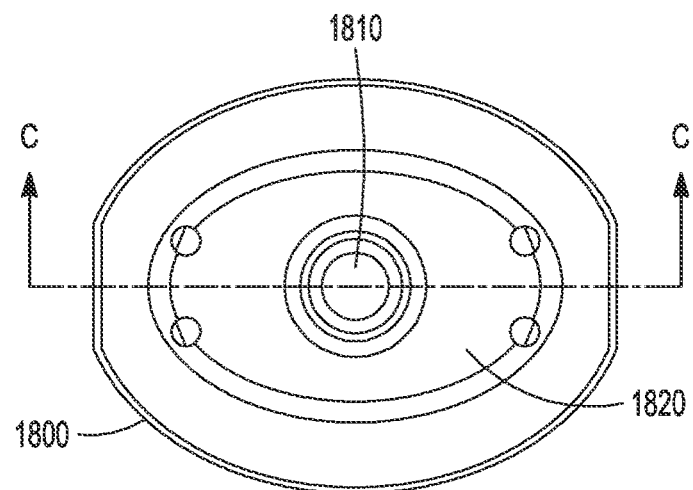
FIGS. 6A and 6B set forth a top cross-sectional view and front cross-sectional view, respectively, of the device of FIG. 4 with the cap partially disengaged.
Figure 6B:
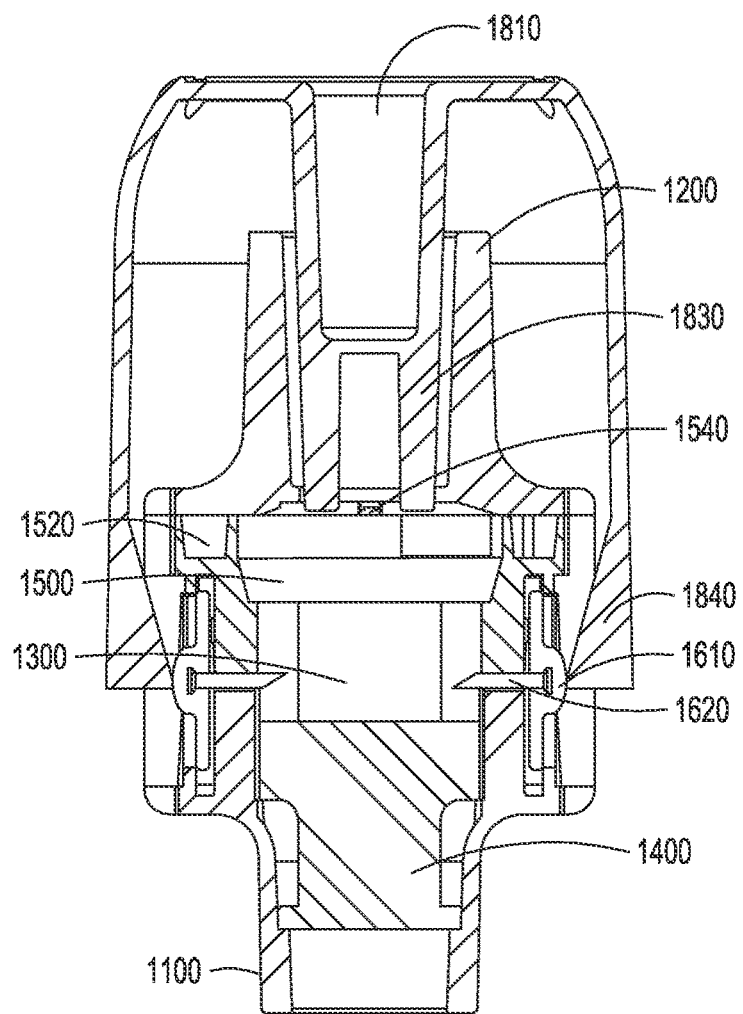

FIGS. 9 through 14 demonstrate a further preferred embodiment configured for single-sided operation, that is to say, activation by negative pressure only. This embodiment is referred to as device 2000. Like parts have like numbering to the parts of device 10 and device 1000. Thus, for example, gas outlet 200 in FIG. 1 is the same as gas outlet 1200 in FIG. 4 and gas outlet 2200 in FIG. 9.

Figure 9:
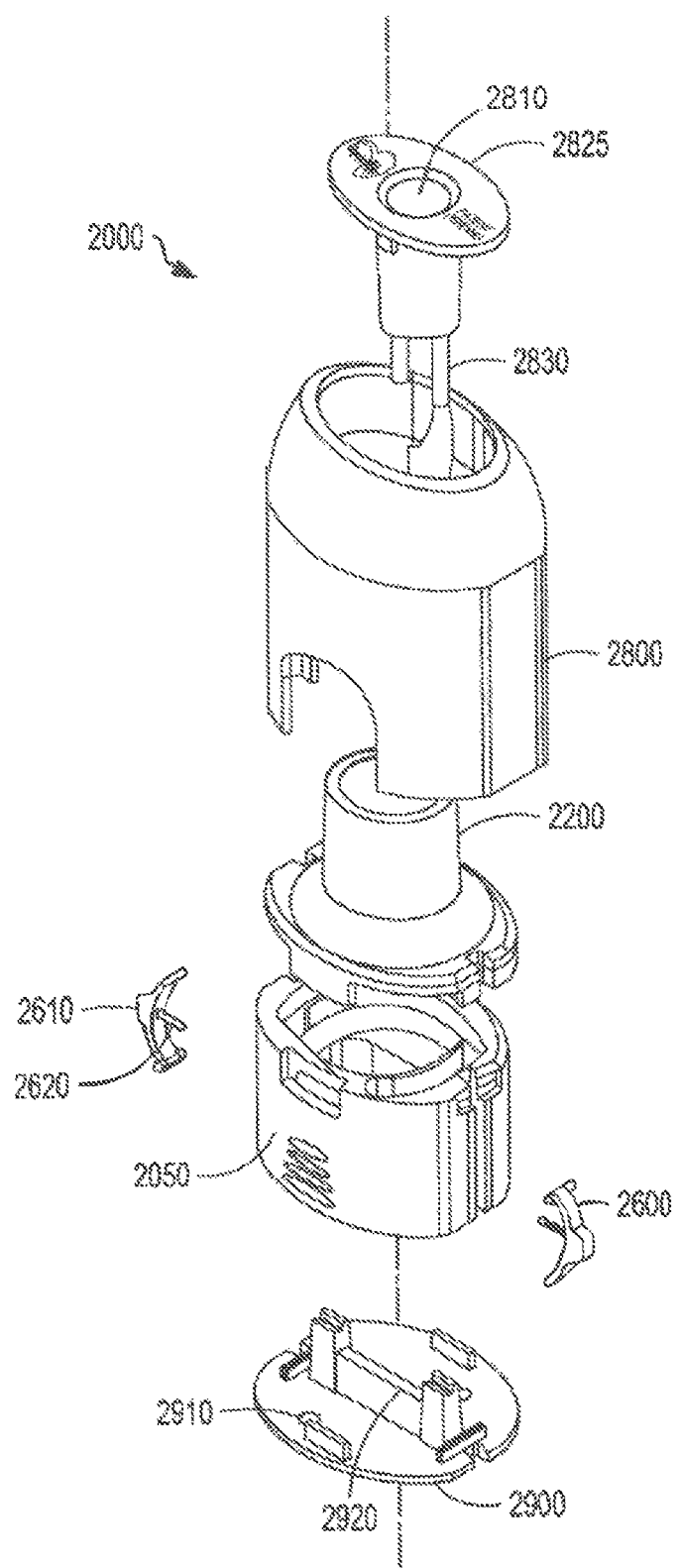
FIG. 9 shows an exploded view of a further embodiment of a device according to the present invention.
Figure 10A:
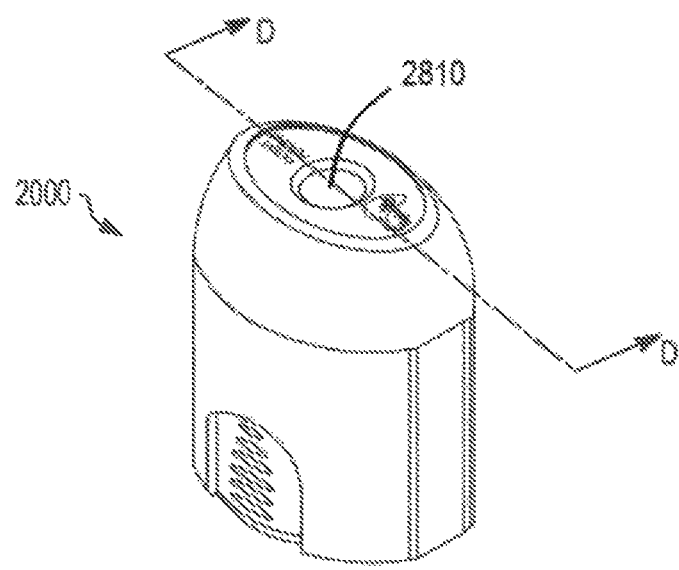
FIGS. 10A and 10B show a perspective view and cross-section view respectively of the device of FIG. 9 in a loaded condition.
Figure 10B:
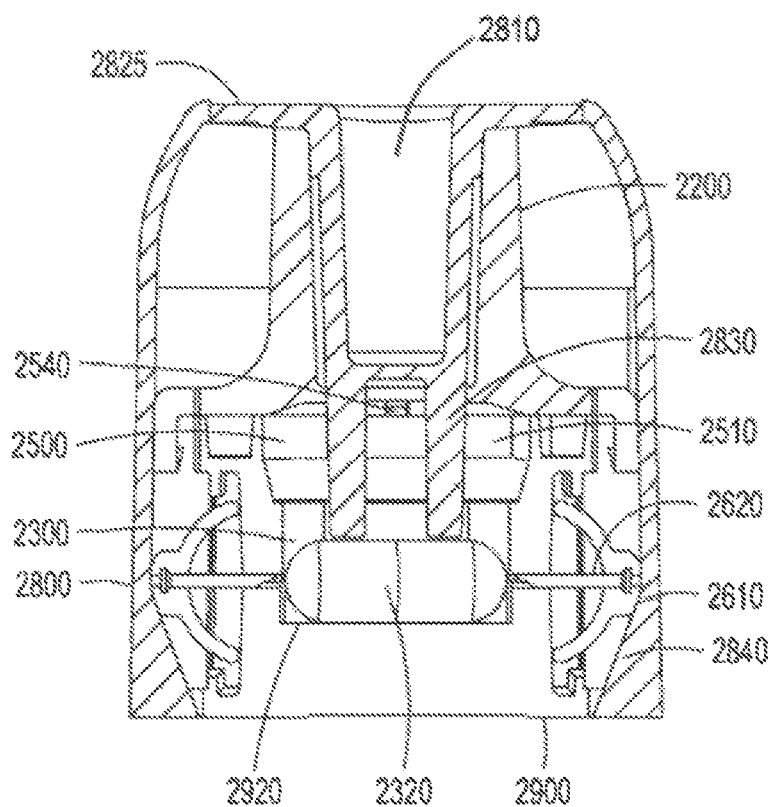

Looking at FIG. 9, device 2000 comprises body 2050; gas outlet 2200; primers 2600; and cap 2800. Unlike devices 10 and 1000, the gas inlet and actuator are replaced by a base 2900. Turning to FIG. 10*b*, the structure previously described is evident with composition receptacle 2300; vortex chamber 2500; but with a composition capsule 2320 shown loaded in the composition receptacle 2300.

FIG. 9 shows an exploded view of device 2000. For simplicity, only those elements that are different from device 10 and device 1000 are described in detail. All other comments made for device 10 and device 1000 apply to device 2000, mutatis mutandis. Instead of a gas inlet the device comprises a base 2900. The base 2900 includes holes 2910 which allow gas (air) to flow into the device in operation. As made clear below, air flows through the holes 2910, composition receptacle 2300, the vortex chamber 2500 and out the gas outlet 2200, when a user inhales.

Looking at the base 2900, apart from holes 2910 it can be seen that there is a capsule seat 2920 that receives a composition capsule 2320, as depicted in FIG. 10*b*.

Looking at cap 2800, it will be seen that there is a cap top 2825, which is movable relative to the cap 2800 as explained below. A well 2810 is formed in the cap top 2825 and a pair of elongate members 2830 extend from the cap top 2825 to hold the composition capsule 2320 in place, as seen clearly in FIG. 10*b*. The elongate members 2830 may be in the form of a pair of prongs, as shown. However, the invention is not limited to a pair of prongs but there could be 1, 3, 4 or some other number of prongs, or some other structure not in the form of prongs that serves the function of holding the composition capsule 2320 in place in the capsule seat 2920.

The structure of device 2000 and the differences from device 10 and 1000 can best be exemplified by explaining the operation by reference to FIGS. 10 to 14. Looking at FIG. 10*a* there is shown device 2000 in what may be called a 'closed', 'delivered', 'loaded' or pre-activation state. The cap 2800 is fully down on the body 2050. In one form, the holes 2910 may be closed by plugs or seals (not shown) that are connected to the cap 2800 to act as a restraint. The plugs must be removed before the cap 2800 can be lifted from the body 2050.

As can be seen in the cross-section of FIG. 10*b*, the composition capsule 2320 is seated in the capsule set 2920, primers 2600 are retracted and cap top 2825 is in place with elongate members 2830 holding composition capsule 2320 in place.

Figure 11A:
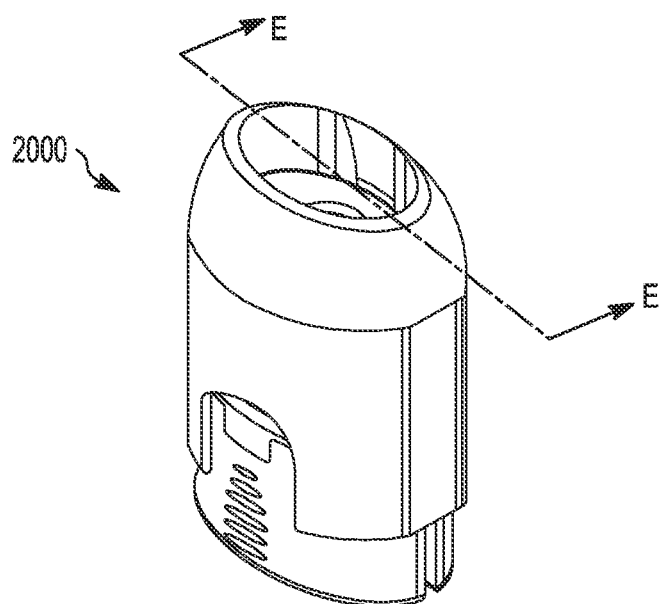
FIGS. 11A and 11B show a perspective view and cross-section view respectively of the device of FIG. 9 being activated.
Figure 11B:
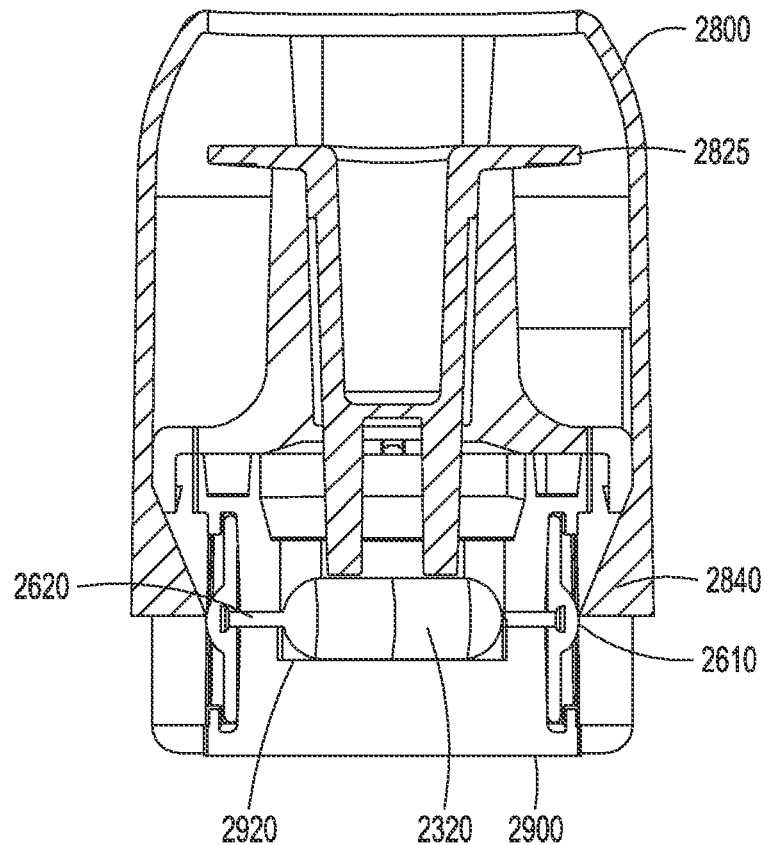

Activation of device 2000 for use occurs by removing cap 2800. This occurs in a number of steps. As shown in FIG. 11*a* and FIG. 11*b*, initially, the cams 2840 impinge upon the cam followers 2610, causing compression of the primer 2600 until the pins 2620 puncture the composition capsule 2320. The cap top 2825 remains in place with the elongate members 2830 holding the composition capsule 2320 against the capsule seat 2920. It will be appreciated that this arrangement has the advantage that the composition capsule 2320 is held in place no matter the orientation of the device 2000, thus ensuring piercing of the composition capsule 2320 by the pins 2620.

Figure 12A:
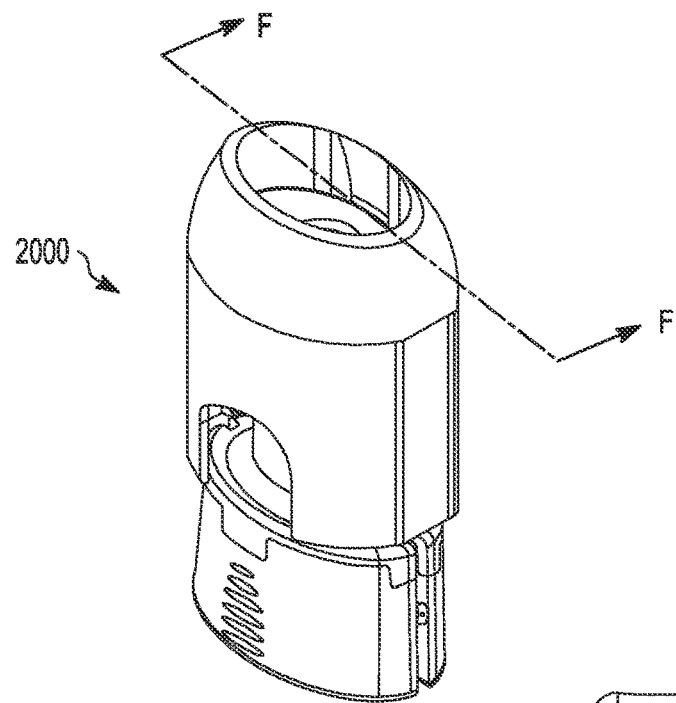
FIGS. 12A and 12B show a perspective view and cross-section view respectively of the device of FIG. 9 in an activated state.
Figure 12B:
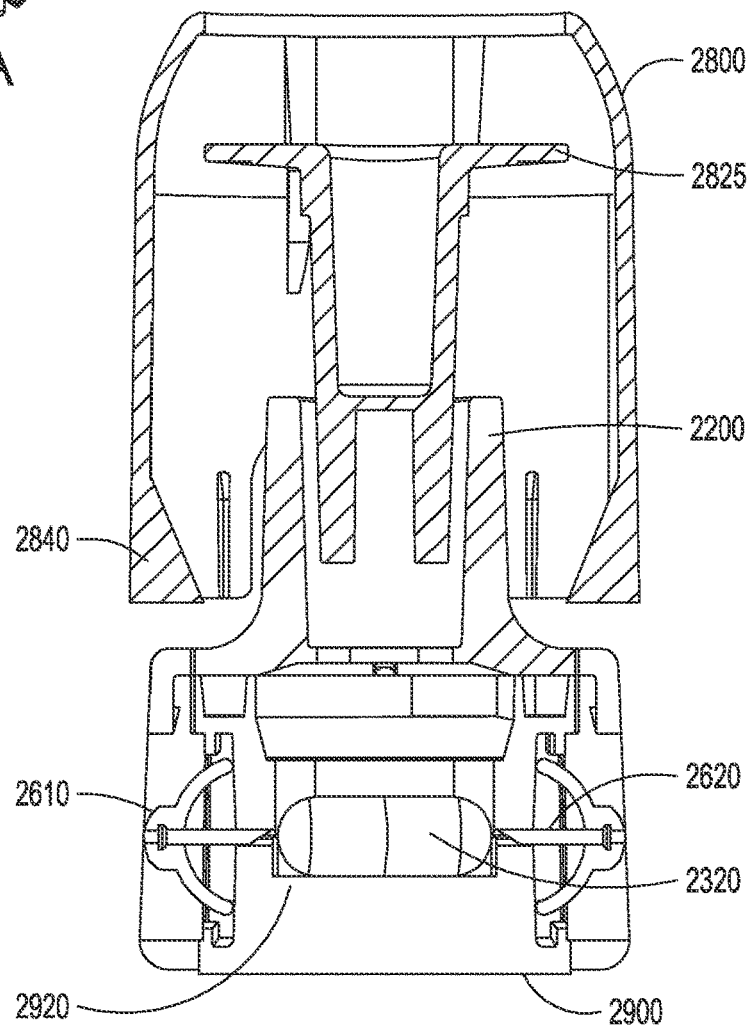
Figure 13A:
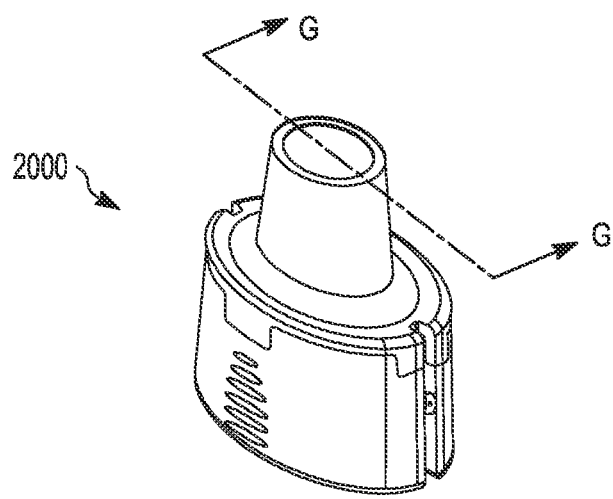
FIGS. 13A and 13B show a perspective view and cross-section view respectively of the device of FIG. 9 in use.
Figure 13B:
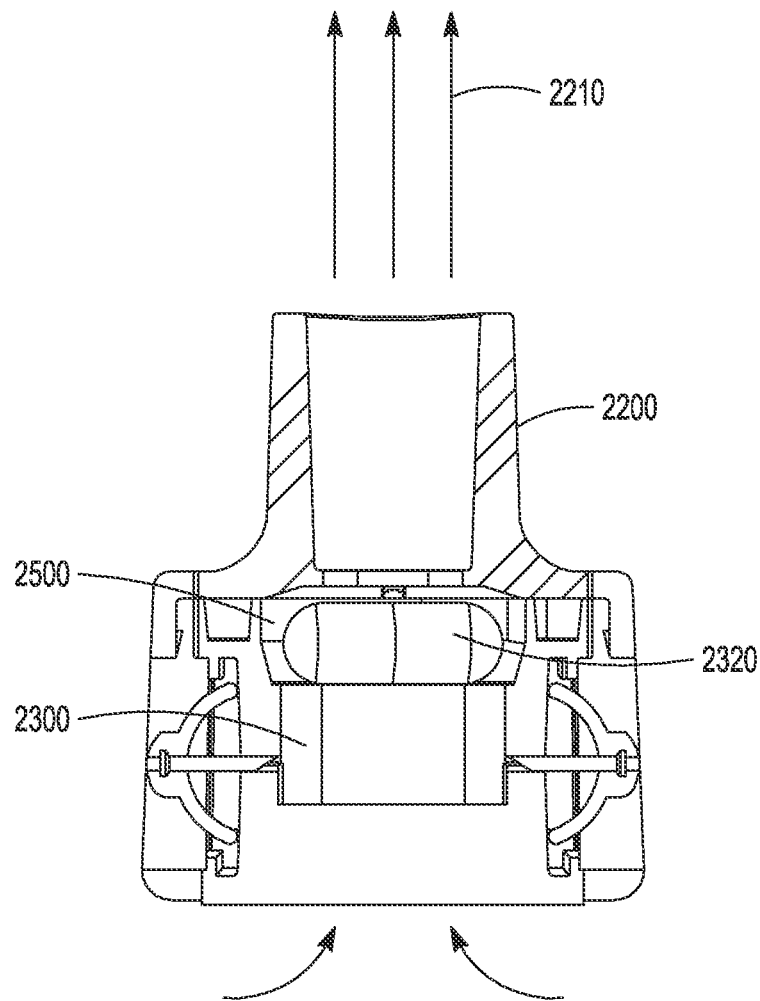

As shown in FIG. 12*a* and FIG. 12*b*, the cap 2800 is continued to be removed from the body 2050 so that immediately after the composition capsule 2320 is pierced the pressure on the elastically deformable primers 2600 is released and the pins 2620 retract. The cap top 2825 now moves with the cap 2800 and is removed, thus permitting access to gas outlet 2200. This may be called the 'open', 'ready' or 'activated' state as the device 2000 is ready for use as shown in FIG. 13*a* and FIG. 13*b*.

As depicted by arrows 2210, inhalation by a user causes a flow of air through the holes 2910, through the composition receptacle 2300 which lifts the composition capsule 2320 into the vortex chamber 2500 where the composition is dispersed in the manner previously described, and hence through the gas outlet 2200 with composition entrained for delivery to the user.

Figure 14:
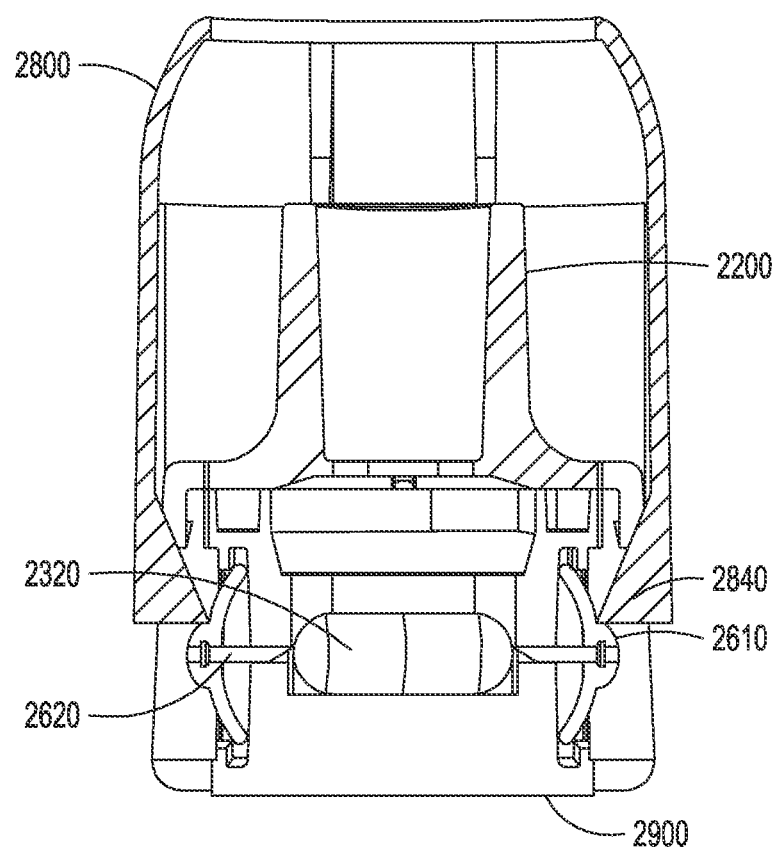
FIG. 14 depicts that the device of FIG. 9 cannot be returned to a loaded condition.

A particular advantage of this embodiment of the invention is that, as shown in FIG. 14, the cap 2800 cannot be replaced on the body 2050 because the primers 2600 are in the way. It should be clear that the automatic puncturing of the composition capsule 2320 is not only applicable only to the embodiment of FIGS. 10 to 14. The embodiment of FIG. 4 to FIG. 9 can be configured in the same way, in which case the outlet end 1420 of the piston 1400 becomes the capsule seat and the cap 1800 is formed in two parts instead of one.

It will be readily appreciated, in view of the above, that devices of this aspect, such as devices 10, 1000 or 2000 can offer advantageous flexibility and/or versatility in use. For example, devices 10, 1000 or 2000 can be used as an inhaler device for self-administration of the composition by the subject. Device 10 or device 1000 can also be used in resuscitation scenarios, where the composition is administered in conjunction with artificial breaths from a caregiver. Device 10 or device 1000 can also be used in hospital scenarios, where the composition is administered by insufflation using a respiratory mask or advanced airway arrangement.

Advantageously, embodiments of devices of this aspect, such as devices 10, 1000 or 2000 can be adjusted or modified to alter dosage in accordance with the subject's particular requirements.

For example, the size and/or number of pins 620/1620/2620 and/or blades of primer 600/1600/2600 can be altered or modified to adjust the rate of delivery of the composition. It will be readily appreciated that a greater number or size of pins or blades will typically allow for a higher rate of release of the composition from dispersion chamber 500/1500/2500, and subsequent delivery to the subject.

By way of further example, the number, position, and/or height of protrusions 540/1540/2540, such as elongate protrusions, radially oriented bumps or protuberances, within dispersion chamber 500/1500/2500, such as on wall 510/1510/2510 or ceiling of vortex chamber 500/1500, can be altered or modified to adjust the rate of delivery of the composition. It will be readily appreciated that, at least wherein the arrangement of protrusions does not substantially inhibit or constrain rotation of a container or capsule within dispersion chamber 500/1500/2500, increasing number and/or height of the protrusions will typically increase release of the composition from dispersion chamber 500/1500/2500, and subsequent delivery to the subject.

Similarly, in embodiments of the device comprising a deagglomerator 700/1700, characteristics of the deagglomerator (e.g. in respect of the flexible member or screen properties) can be modified or adjusted to adjust the rate of composition delivery.

Advantageously, embodiments such as device 10 or device 1000 are typically reliable in use in respect of delivery from containers or capsules.

For example, the arrangement wherein configuration of actuator 400/1400 between the first configuration and the second configuration both (a) moves the container or capsule from composition receptacle 300/1300 to dispersion chamber 500/1500; and (b) is facilitated and maintained by gas flow between the gas inlet 100/1100 and the gas outlet 200/1200, can be effective for preventing or at least avoiding unwanted displacement or lack of displacement, e.g. 'sticking', of the container or capsule.

Additionally, embodiments such as devices 10, 1000 or 2000 particularly wherein composition receptacle 300/130/2300 is formed to fittingly receive the container or capsule, can typically be primed and used when positioned in any orientation, with limited or no change in performance.

Advantageously, as hereinabove described, embodiments such as devices 10, 1000, 2000 typically feature a substantially sealed or airtight gas flow path through body 50/1050/2050 from inlet 100/1100/2910 to outlet 200/1200/2200. It will be appreciated that such a sealed flow path substantially prevents, or at least constrains, unwanted escape or leakage of the composition.

Advantageously, embodiments such as devices 10, 1000 or 2000 particularly embodiments comprising a dosage tracker, allow estimation of the dose of the composition delivered to the subject. It will be appreciated that this can assist in dosage reliability and can decrease the likelihood of under or over dosing, and/or warn a user if under or overdosing occurs.

Further, device 1000/2000 provides distinct advantages in easy priming of the device 1000/2000 for use simply by removal of the cap 1800/2800.

The above is a non-limiting listing of some typical advantages of exemplary embodiments.

A further aspect of this invention provides a method of administering a composition to the airway of a subject using a device of the previous aspect, such as device 10/1000/2000.

A related aspect provides a method of treating or preventing a condition in a subject by administering an effective amount of composition to the airway of a subject using a device of the previous aspect, such as device 10/1000/2000. Typically, the subject according to these aspect is a human subject.

As will be readily appreciated by the skilled person, according to these aspects, a suitable composition can be selected for administration to a particular subject, including for a particular therapeutic purpose in relation to a particular condition.

Generally, compositions administered as described herein may include any suitable medicament for administering to the subject's airway, in accordance with the subject's condition and medical requirements. As hereinabove described, typically the composition will be a dry powder, and may be in the form of one or more pure, or substantially pure, active ingredients. The composition may alternatively include one or more pharmaceutically acceptable components in addition to one or more active ingredients, e.g. fillers, excipients, or diluents, as are well known in the art.

As will be appreciated by the skilled person, the size of particles of a dry powder composition administered to a subject's airways can affect the therapeutic efficacy of the dry powder. Typically, the administered microparticles will have a d50 or Mean Mass Aerodynamic Diameter (MMAD) less than 6 µm. As will be understood by the skilled person "d50" or "D50" refers to the value that the particle diameter of 50% by mass of a particulate sample is less than. The d50 particle MMAD is preferably between about 0.5 and about 20 µm, including about: 1, 2, 3, 4, 5, 6, 7, 8, 9, 10, 11, 12, 13, 14, 15, 16, 17, 18, and 19 µm, more preferably between about 0.5 and 10 µm, and even more preferably between 1 and 6 µm, including about: 1.5, 2, 2.5, 3, 3.5, 4, 4.5, 5 and 5.5 µm. It will be appreciated that, in embodiments wherein device 10 comprises deagglomerator 700, the preceding values refer to particle size after dispersion into the flow of gas and/or after passing through the deagglomerator 700.

Examples of active agents which may be delivered according to the present invention include beta-2-agonists, steroids such as glucocorticosteroids (preferably anti-inflammatories), anti-cholinergics, leukotriene antagonists, leukotriene synthesis inhibitors, pain relief drugs generally, such as analgesics and anti-inflammatories (including both steroidal and non-steroidal anti-inflammatories), cardiovascular agents such as cardiac glycosides, respiratory drugs, anti-asthma agents, bronchodilators, anti-cancer agents, alkaloids (e.g. ergot alkaloids) or triptans such as can be used in the treatment of migraine, drugs (for instance sulphonylureas) useful in the treatment of diabetes type I and II and related disorders, sleep inducing drugs including sedatives and hypnotics, psychic energizers, appetite suppressants, anti-arthritics, anti-malarials, anti-epileptics, anti-thrombotics, anti-hypertensives, anti-arrhythmics, anti-oxidants, anti-depressants, anti-psychotics, auxiolytics, anti-convulsants, anti-emetics, anti-infectives, anti-histamines, anti-fungal and anti-viral agents, drugs for the treatment of neurological disorders such as Parkinson's disease (dopamine antagonists), drugs for the treatment of alcoholism and other forms of addiction, drugs such as vasodilators for use in the treatment of erectile dysfunction, muscle relaxants, muscle contractants, opioids, stimulants, tranquilizers, antibiotics such as macrolides, aminoglycosides, fluoroquinolones and beta-lactams, vaccines, cytokines, growth factors, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents and mixtures of the above (for example the asthma combination treatment containing both steroid and beta-agonist).

The active agent may fall into one of a number of structural classes, including but not limited to small molecules (including insoluble small molecules), peptides, polypeptides, proteins, polysaccharides, steroids, nucleotides, oligonucleotides, polynucleotides, fats, electrolytes, and the like. Specific examples include the beta-2-agonists salbutamol (e.g. salbutamol sulphate) and salmeterol (e.g. salmeterolxinafoate), the steroids budesonide and fluticasone (e.g. fluticasone propionate), the cardiac glycoside digoxin, the alkaloid anti-migraine drug dihydroergotaminemesylate and other alkaloid ergotamines, the alkaloid bromocriptine used in the treatment of Parkinson's disease, sumatriptan, rizatriptan, naratriptan, frovatriptan, almotriptan, zolmatriptan, morphine and the morphine analogue fentanyl (e.g. fentanyl citrate), glibenclamide (a sulphonyl urea), benzodiazepines such as vallium, triazolam, alprazolam, midazolam and clonazepam (typically used as hypnotics, for example to treat insomnia or panic attacks), the anti-psychotic agent risperidone, apomorphine for use in the treatment of erectile dysfunction, the anti-infective amphotericin B, the antibiotics tobramycin, ciprofloxacin and moxifloxacin, nicotine, testosterone, the anti-cholenergic bronchodilator ipratropium bromide, the bronchodilator formoterol, monoclonal antibodies and the proteins LHRH, insulin, human growth hormone, calcitonin, interferon (e.g. beta- or gamma-interferon), EPO and Factor VIII, as well as in each case pharmaceutically acceptable salts, esters, analogues and derivatives (for instance prodrug forms) thereof.

Additional examples of potentially suitable active agents include but are not limited to aspariginase, amdoxovir (DAPD), antide, becaplermin, calcitonins, cyanovirin, denileukindiftitox, erythropoietin (EPO), EPO agonists, domase alpha, erythropoiesis stimulating protein (NESP), coagulation factors such as Factor Vila, Factor VIII, Factor IX, von Willebrand factor; ceredase, cerezyme, alpha-glucosidase, collagen, cyclosporin, alpha defensins, beta defensins, exedin-4, granulocyte colony stimulating factor (GCSF), thrombopoietin (TPO), alpha-1 proteinase inhibitor, elcatonin, granulocyte macrophage colony stimulating factor (GMCSF), fibrinogen, filgrastim, growth hormones, growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau; interleukins and interleukin receptors such as interleukin-1 receptor, interleukin-2, interleukin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues, amylin, C-peptide, somatostatin, somatostatin analogs including octreotide, vasopressin, follicle stimulating hormone (FSH), influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1 endothelial growth factors, parathyroid hormone (PTH), glucagon-like peptide, somatotropin, thymosin alpha 1, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosponates, respiratory syncytial virus antibody, cystic fibrosis transmembrane regulator (CFTR) gene, deoxyreibonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, afeliomomab, basiliximab, daclizumab, infliximab, ibritumomabtiuexetan, mitumomab, muromonab-CD3, iodine 131 tositumomab conjugate, olizumab, rituximab, and trastuzumab (herceptin), amifostine, amiodarone, aminoglutethimide, amsacrine, anagrelide, anastrozole, asparaginase, anthracyclines, bexarotene, bicalutamide, bleomycin, buserelin, busulfan, cabergoline, capecitabine, carboplatin, carmustine, chlorambucin, cisplatin, cladribine, clodronate, cyclophosphamide, cyproterone, cytarabine, camptothecins, 13-cis retinoic acid, all transretinoic acid; dacarbazine, dactinomycin, daunorubicin, dexamethasone, diclofenac, diethylstilbestrol, docetaxel, doxorubicin, epirubicin, estramustine, etoposide, exemestane, fexofenadine, fludarabine, fludrocortisone, fluorouracil, fluoxymesterone, flutamide, gemcitabine, epinephrine, L-Dopa, hydroxyurea, idarubicin, ifosfamide, imatinib, irinotecan, itraconazole, goserelin, letrozole, leucovorin, levamisole, lomustine, mechlorethamine, medroxyprogesterone, megestrol, melphalan, mercaptopurine, methotrexate, metoclopramide, mitomycin, mitotane, mitoxantrone, naloxone, nicotine, nilutamide, octreotide, oxaliplatin, pamidronate, pentostatin, pilcamycin, porfimer, prednisone, procarbazine, prochlorperazine, ondansetron, raltitrexed, sirolimus, streptozocin, tacrolimus, tamoxifen, temozolomide, teniposide, testosterone, tetrahydrocannabinol, thalidomide, thioguanine, thiotepa, topotecan, tretinoin, valrubicin, vinblastine; vincristine, vindesine, vinorelbine, dolasetron, granisetron; formoterol, fluticasone, leuprolide, midazolam, alprazolam, amphotericin B, podophylotoxins, nucleoside antivirals, aroyl hydrazones, sumatriptan; macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicllinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidineisethiouate, albuterolsulfate; lidocaine, metaproterenolsulfate, beclomethasonediprepionate, triamcinolone acetamide, budesonide acetonide, fluticasone, ipratropium bromide, flunisolide, cromolyn sodium, and ergotamine tartrate; taxanes such as paclitaxel; SN-38; tyrphostines.

Other agents that may be used include: Linezolid; Treprostinol optionally in combination with a PDE5 Inhibitor;

Oxyntomodulin; and Palonosetron optionally in combination with a, preferably high potency, NK1 antagonist.

It will be understood that the above exemplary active agents encompass, as applicable, analogues, agonists, antagonists, inhibitors, isomers, and pharmaceutically acceptable salt forms thereof. In regard to peptides and proteins, the invention is intended to encompass synthetic, recombinant, native, glycosylated, non-glycosylated, and biologically active fragments and analogues thereof.

In some typical embodiments, the composition includes one or more active agents selected from adrenaline, glucose, glucagon, naloxone, insulin or the like.

In some typical embodiments, the composition includes microparticles, nanoparticles, microcapsules, nanocapsules, microspheres, and/or nanospheres of adrenaline and/or atropine for the treatment of cardiac failure, cardiac dysfunction, cardiac arrest, anaphylaxis, drug overdose or the like.

In some typical embodiments the composition includes particulate glucose and/or glucagon for the treatment of hypoglycaemia, diabetes induced coma or the like. In embodiments, the dry powder includes particulate benzodiazepine, phenytoin or anti-seizure medications for the treatment of seizure.

In some typical embodiments, the composition includes one or more agents for inducing an immune response, such as one or more vaccines. In embodiments, the dry powder includes a measles vaccine, for inducing an immune response to, or immunising against, measles. In embodiments, the dry powder includes a Hepatitis B vaccine, for inducing an immune response to, or immunising against, Hepatitis B. In embodiments, the dry powder includes an influenza vaccine, for inducing an immune response to, or immunising against, influenza.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. The invention is intended to embrace all alternatives, modifications, and variations of the present invention that have been discussed herein, and other embodiments that fall within the spirit and scope of the above described invention.

The invention claimed is:

1. A device for delivery of a composition to an airway of a subject, the device comprising:
   in fluid communication:
      a gas inlet;
      a gas outlet;
      a composition receptacle adapted to receive a composition capsule containing the composition; and
      a dispersion chamber; and
   one or more primers each comprising a cam follower and an associated pin or blade; and
   a cap comprising one or more cams which are located so as to engage with and displace the respective primer to pierce the composition capsule upon removal of the cap,
   wherein the cap comprises a cap top, movable relative to the cap, having one or more elongate members extending from the cap top and adapted to hold the composition capsule in place.

2. The device of claim 1, wherein the one or more primers is two primers, each of which comprises a cam follower connected to a pin or blade.

3. The device of claim 1, wherein the cam follower is biased to return to its starting position.

4. The device of claim 1, wherein the cam follower of each of the one or more primers prevents the cap from being replaced once removed.

5. The device of claim 1, wherein the dispersion chamber is adapted to receive the composition for delivery to the subject and to disperse the composition into gas flow between the gas inlet and the gas outlet, for delivery to the airway of the subject.

6. The device of claim 1, wherein the dispersion chamber is adapted to promote rotational movement or spinning of the composition capsule within the dispersion chamber.

7. The device of claim 1, wherein the dispersion chamber is continuous with one or more chamber ports through which gas flows between the gas inlet and the gas outlet.

8. The device of claim 1, wherein the dispersion chamber comprises one or more protrusions projecting from a surface thereof.

9. The device of claim 1, further comprising a deagglomerator located substantially adjacent to the dispersion chamber and in fluid communication with the gas inlet, gas outlet, composition receptacle and dispersion chamber.

10. The device of claim 9, wherein the deagglomerator is a screen or mesh.

11. The device of claim 1, wherein the gas inlet is in the form of a base having one or more holes for ingress of gas and a capsule seat adapted to locate the composition capsule in the composition receptacle.

12. The device of claim 1, wherein the composition capsule is held in place for piercing by the one or more primers between a capsule seat formed in a base comprising the gas inlet and one or more elongate members extending from the cap top of the cap.

13. The device of claim 1, wherein the gas outlet is a mouthpiece.

14. A method of administering a composition to the airway of a subject using the device of claim 1 when loaded with a composition capsule substantially inside the composition receptacle, including the steps of:
   moving the cap so that cams on the cap engage cam followers on the one or more primers thereby causing the one or more primers to pierce or cut the composition capsule;
   removing the cap so as to uncover the gas outlet and release the one or more primers;
   connecting the gas outlet with the airway of the subject; and
   providing gas flow between the gas inlet to the gas outlet, such that the composition is delivered by the gas flow to the airway of the subject via the gas outlet and thereby administer the composition to the airway of the subject.

15. The method of claim 14, wherein inhalation through the gas outlet by a subject causes gas flow from the gas inlet that moves the composition capsule from the composition receptacle to the dispersion chamber.

16. The method of claim 14, wherein the cap cannot be replaced once removed.

17. The device of claim 1, wherein the one or more elongate members extend from the cap top to be adjacent the composition capsule.

18. A device for delivery of a composition to an airway of a subject, the device comprising:

in fluid communication:
  - a gas inlet;
  - a gas outlet;
  - a composition receptacle adapted to receive a composition capsule containing the composition; and
  - a dispersion chamber; and
  - one or more primers each comprising a cam follower and an associated pin or blade; and
  - a cap comprising one or more cams which are located so as to engage with and displace the respective primer to pierce the composition capsule upon removal of the cap, wherein the cap comprises a cap top, movable relative to the cap, having one or more elongate members extending from the cap top to be adjacent the composition capsule, and wherein initial movement of the cap away from the cap top causes displacement of the respective primer prior to the one or more elongate members being moved from their position adjacent the composition capsule.

19. The device of claim 18, further comprising a deagglomerator located substantially adjacent to the dispersion chamber and in fluid communication with the gas inlet, gas outlet, composition receptacle and dispersion chamber, wherein the one or more elongate members extend from the cap top through the deagglomerator to be adjacent the composition capsule.

* * * * *